United States Patent
Glynn

(10) Patent No.: US 10,029,054 B2
(45) Date of Patent: Jul. 24, 2018

(54) LOWER BODY CAVITY TREATMENT METHODS AND DEVICES USING CARBON DIOXIDE AND SALINE

(71) Applicant: Kenneth P. Glynn, Flemington, NJ (US)

(72) Inventor: Kenneth P. Glynn, Flemington, NJ (US)

(73) Assignee: CLOVER HILL HEALTHCARE, INC., Flemington, NJ (US)

( * ) Notice: Subject to any disclaimer, the term of this patent is extended or adjusted under 35 U.S.C. 154(b) by 76 days.

(21) Appl. No.: 14/999,741

(22) Filed: Jun. 22, 2016

(65) Prior Publication Data
US 2017/0368272 A1  Dec. 28, 2017

(51) Int. Cl.
| | |
|---|---|
| *A61K 9/34* | (2006.01) |
| *A61M 11/00* | (2006.01) |
| *A61K 33/00* | (2006.01) |
| *A61K 9/00* | (2006.01) |
| *A61K 9/08* | (2006.01) |
| *A61K 33/14* | (2006.01) |
| *A61K 45/06* | (2006.01) |
| *A61K 9/46* | (2006.01) |
| *A61M 39/22* | (2006.01) |

(52) U.S. Cl.
CPC ......... *A61M 11/007* (2014.02); *A61K 9/0007* (2013.01); *A61K 9/0031* (2013.01); *A61K 9/0034* (2013.01); *A61K 9/08* (2013.01); *A61K 33/00* (2013.01); *A61K 33/14* (2013.01); *A61K 45/06* (2013.01); *A61M 39/22* (2013.01); *A61M 2205/3334* (2013.01); *A61M 2210/1042* (2013.01); *A61M 2210/1078* (2013.01); *A61M 2210/1475* (2013.01)

(58) Field of Classification Search
CPC ........ A61K 9/0034; A61M 2210/1078; A61M 2210/1475
See application file for complete search history.

(56) References Cited

U.S. PATENT DOCUMENTS

| | | | | |
|---|---|---|---|---|
| 9,272,036 B2 * | 3/2016 | Glynn | ................ | A61K 33/00 |
| 2013/0280348 A1 * | 10/2013 | Glynn | ................ | A61K 33/00 |
| | | | | 424/700 |
| 2013/0281917 A1 * | 10/2013 | Glynn | ................ | A61K 33/00 |
| | | | | 604/24 |
| 2013/0319412 A1 * | 12/2013 | Glynn | ................ | A61M 15/08 |
| | | | | 128/203.21 |

(Continued)

*Primary Examiner* — Aarti B Berdichevsky

(57) ABSTRACT

A method of treatment for mixed carbon dioxide, carbonic acid, saline and optional active additives for treating lower body cavity ailments includes delivery of dosage of the treatment at specified flow rates, using a) main housing having a hollow central area containing the dosage; b) a dosage dispenser head located at the distal end of the main housing, and having at least one flow channel for movement of the dosage from the main housing through the dosage dispenser head and to external of the dosage dispenser head; c) a dosage release control component located between the main housing and the dosage dispenser head to permit flow of the dosage through the dosage dispenser head in response to increased pressure against the dosage; and d) a pressure-changing moveable component on the main housing.

26 Claims, 10 Drawing Sheets

(56) References Cited

U.S. PATENT DOCUMENTS

| | | | | |
|---|---|---|---|---|
| 2015/0010654 A1* | 1/2015 | Arnold | ................ | A61K 9/0031 |
| | | | | 424/717 |
| 2015/0182479 A1* | 7/2015 | Glynn | ................ | A61K 31/155 |
| | | | | 514/634 |
| 2016/0325080 A1* | 11/2016 | Glynn | .................... | A61M 11/00 |
| 2017/0224936 A1* | 8/2017 | Glynn | ................ | A61M 11/007 |
| 2017/0360831 A1* | 12/2017 | Glynn | .................... | A61K 33/14 |

* cited by examiner

FIGURE 2

AILMENTS/ PURPOSES

- Vaginal area ailments —17
- Intestinal area ailments —19
- Urinary tract ailments —21
- Flushes, cleansings, douches, enemas, anti-infections, medicine deliveries —23

DURATION OF THERAPEUTIC NON-NASAL DOSAGE —30

- 1/2 to 20 seconds —29
- 2 to 15 seconds —31
- 5 to 10 seconds —33

FIGURE 5

```
       FLOW RATES

• Up to 25 cc/sec
 • 0.2 cc/sec to 10 cc/sec       ⟋ 50
 • 0.4 cc/sec to 4 cc/sec
 • 0.4 cc/sec to 2 cc/sec
 • 10 cc/sec
```

FIGURE 6

```
 PERCENTAGE OF CO₂ PR
  IN DOSAGE (By Wt.)

• Not exceed 1% CO₂             ⟋ 60
 • 0.05 to 1.0 % CO₂
 • 0.2 to 0.8 % CO₂
 • 0.2 to 0.6 % CO₂
```

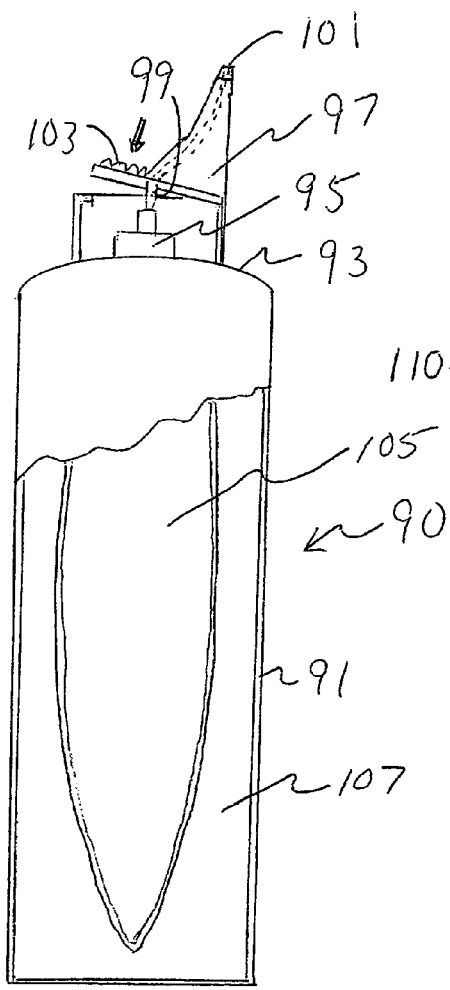
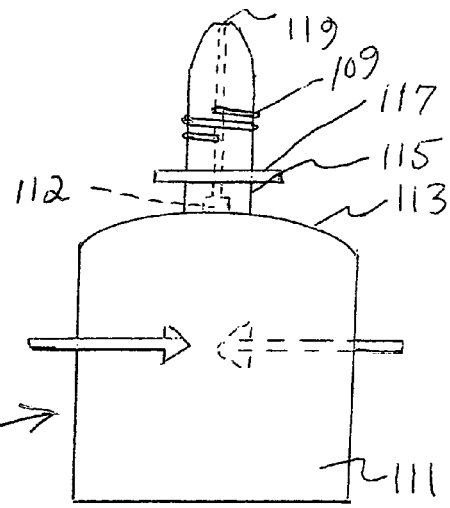
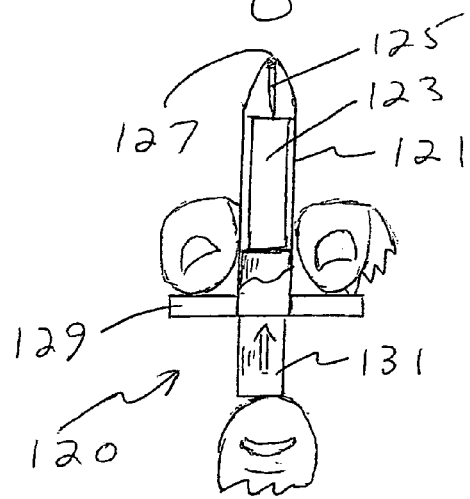
Figure 8
Figure 9
Figure 10

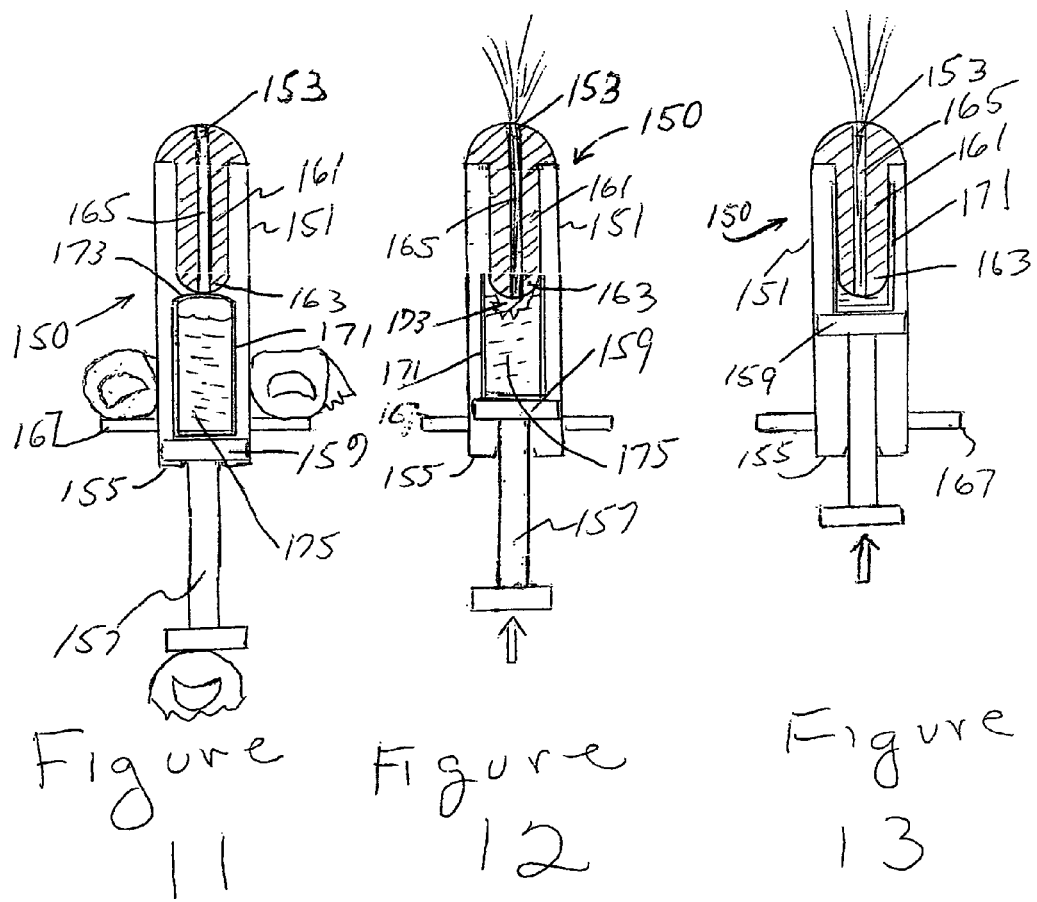

us 10,029,054 B2

LOWER BODY CAVITY TREATMENT METHODS AND DEVICES USING CARBON DIOXIDE AND SALINE

REFERENCE TO RELATED APPLICATIONS

The present application is a continuation-in-part application of of copending U.S. patent application Ser. No. 13/506,426, by the same inventor herein, namely, Kenneth P. Glynn, filed on Apr. 18, 2012 titled "CARBON DIOXIDE AND SALINE NASAL DELIVERY METHODS AND TREATMENTS"; and the present application is a continuation-in-part application of copending U.S. patent application Ser. No. 13/507,112, by the same inventor herein, namely, Kenneth P. Glynn, filed on Jun. 4, 2012 titled "NASAL TREATMENT DELIVERY DEVICE FOR MIXED CARBON DIOXIDE AND SALINE TREATMENTS", which will issue on Jun. 21, 2016 as U.S. Pat. No. 9,370,632.

BACKGROUND OF INVENTION a. Field of Invention

The present invention relates generally to healthcare, and specifically to the treatment of ailments involving lower body cavities. More specifically, the present invention relates to delivery devices for treatments with mixtures of carbon dioxide, carbonic acid and saline, with or without other active ingredients, as well as methods of treatment utilizing these devices. Thus, the present invention is directed to treating lower body cavities with effervescent saline, with or without additional actives. As used herein the phrase "lower body cavity" is meant to refer to specific areas of the body, namely, urinary, vaginal and intestinal. Thus, the present invention method involves treatment of the anal area, the bowels, the urinary tract, and the vaginal cavity and related aspects of the female urinary and reproductive areas. With regard to intestinal treatment, in some embodiments, the present invention is an enema. With regard to vagina treatment, in some embodiments, the present invention is a douche. In yet other embodiments, the present invention methods and devices are used for drug delivery, before, at, after or without surgery. One example would be the rectal delivery of analgesics.

b. Description of Related Art

The following patents and applications are representative of various types of medicine delivery methods and devices:

U.S. Pat. No. 8,007,842 B2 to Rau describes a composition for providing aromatherapy, and in particular, symptomatic relief of nasal and sinus congestion in unit dosage format. The composition includes a penetrating aromatic vapor whose release from a preparation of warm water is augmented by an effervescent component which reacts in the warm water to promote release of the aromatic fragrance, or sustained over time by tableting or gelatin encapsulation. As the fragrance is inhaled, symptomatic relief is obtained. The composition of matter may be rendered ingestible, so that the warm water containing the composition is consumed following inhalation. In preferred embodiments, the release of the penetrating aromatic fragrance persists over time.

U.S. Pat. No. 7,959,597 B2 to Baker et al. describes an irrigation and aspiration system. The system can be configured to aspirate and irrigate alone, sequentially or concurrently. The system can be configured to aspirate and irrigate the nasal cavity. The system can be manually controlled. The system can have removable and easily cleanable reservoirs for aspirant and irrigant.

U.S. Pat. No. 7,858,650 B2 to Yamamoto et al. describes a medicinal composition for inhalation containing a continuous-release type pro-drug of an EP2 agonist which topically exhibits a prolonged broncho-dilating and anti-inflammatory effects. Namely, the medicinal composition for inhalation containing a continuous-release type pro-drug of an EP2 agonist is useful as a safe preventive and/or a remedy for respiratory diseases (for example, asthma, pulmonary injury, pulmonary fibrosis, pulmonary emphysema, bronchitis, chronic obstructive pulmonary disease, adult respiratory distress syndrome, cystic fibrosis, pulmonary hypertension or the like) without causing any systemic effect such as lowering blood pressure. Thus, a safe and useful remedy for respiratory diseases is provided.

U.S. Pat. No. 7,845,348 B2 to Rasor et al. describes apparatus, methods, and kits for treating symptoms associated with common ailments, such as headaches, rhinitis, asthma, epilepsy, nervous disorders and the like. The apparatus comprises dispensers for carbon dioxide and other therapeutic gases. The methods comprise delivering small volumes of these gases to patients in a manner where the gas infuses into a body region in order to bathe the mucous membranes therein. It has been found that even very short exposure of patients to small volumes and high concentrations of such gases can provide significant relief from symptoms.

U.S. Pat. No. 7,836,883 B2 to Rasor et al. describes apparatus, methods, and kits for treating symptoms associated with common ailments, such as headaches, rhinitis, asthma, epilepsy, nervous disorders and the like. The apparatus comprises dispensers for carbon dioxide and other therapeutic gases. The methods comprise delivering small volumes of these gases to patients in a manner where the gas infuses into a body region in order to bathe the mucous membranes therein. It has been found that even very short exposure of patients to small volumes and high concentrations of such gases can provide significant relief from symptoms.

U.S. Pat. No. 7,827,986 B2 to Rasor et al. describes apparatus, methods, and kits for treating symptoms associated with common ailments, such as headaches, rhinitis, asthma, epilepsy, nervous disorders and the like. The apparatus comprises dispensers for carbon dioxide and other therapeutic gases. The methods comprise delivering small volumes of these gases to patients in a manner where the gas infuses into a body region in order to bathe the mucous membranes therein. It has been found that even very short exposure of patients to small volumes and high concentrations of such gases can provide significant relief from symptoms.

U.S. Pat. No. 7,017,573 B1 to Rasor et al. describes apparatus, methods, and kits for treating symptoms associated with common ailments, such as headaches, rhinitis, asthma, epilepsy, nervous disorders and the like. The apparatus comprises dispensers for carbon dioxide and other therapeutic gases. The methods comprise delivering small volumes of these gases to patients in a manner where the gas infuses a body region in order to bathe the mucous membranes therein. It has been found that even very short exposure of patients to small volumes and high concentrations of such gases can provide significant relief from symptoms.

U.S. Pat. No. 5,609,581 to Fletcher, et al. describes the combination comprising a container for a product having a puncturable diaphragm at one end thereof, an applicator of elongated parabolic shape including means for detachably mounting it on the container, an internal piercing element in the applicator aligned with the diaphragm and a plurality of discharge openings in the applicator, the applicator actuatable between an unarmed position wherein the piercing element is spaced from the diaphragm in an armed position where it punctures the diaphragm to permit discharge of the contents through the piercing element and the discharge openings in the applicator.

U.S. Pat. No. 3,221,945 B1 to Davis describes medication dispensers of the squeeze bottle type for treatment of nasal and sinus infections that have specific valving with resilient wall bottles.

United States Patent Application No. 2012/0179122 A1 to Eliat et al describes device for applying an ophthalmologic medicament to a patient's eye. The device comprises spectacles defined by a frame and at least one lens; at least one container adapted for accommodating the ophthalmologic medicament; the container is incorporated into the frame; dosing mechanism adapted to control doses of the medicament; and at least one nozzle in a fluid interconnection with the medicament container; the nozzle is secured mechanically to the frame; the nozzle is adapted for providing a medicament mist flow. The nozzle is placed in front of a peripheral portion of a patient's eye slot and adapted to provide the mist flow in front of the patient's eye.

United States Patent Application No. 2011/0233232 A1 to Greiner-Perth et al describes a discharging device for pharmaceutical liquids having an actuator for carrying out a discharging operation of a pharmaceutical liquid. A first subordinate unit of the actuator has a discharge orifice, and a second subordinate unit is displaceable relative to the first subordinate unit for carrying out the discharging operation. The two subordinate units together delimit a buffer chamber from which a liquid passageway leads to the discharge orifice. A liquid-containing bag is accommodated in the buffer chamber and has film-like walls. The actuator and the bag are coordinated such that displacement of the subordinate units of the actuator relative to each other causes opening of the bag and reduction in the volume of the buffer chamber with consequent volume reduction of the liquid-containing bag and discharge of liquid through the discharge orifice.

United States Patent Application No. 2010/0305130 A1 to Phillips describes a single-use sprayer for nasal anesthesia is disclosed. The single-use sprayer includes a single dose of anesthetic and a delivery system adapted to dispense the single dose of anesthetic into a nostril. The single-use sprayer prevents patient-to-patient contamination, is easy to use and allows for self-administration, and has a simple, disposable configuration so as to lower the production cost.

United States Patent Application No. 2008/0169047 A1 to Connolly et al. describes a hand-held, low-flow dispenser which comprises an enclosure holding a gas cartridge. A spring-biased needle is advanced to puncture a septum on the gas cartridge, and a separate spring-biased ball valve is used to turn the resulting gas flow off and on as well as to control the flow rate.

United States Patent Application No. 2008/0114310 A1 to Kamen, et al. describes a method for packaging an agent for delivery within a body cavity. A reservoir within a package contains a specified quantity of the agent and is either contiguous with, or coupled to, a dispensing node such as a swab. Depth of insertion of the dispensing node into the body cavity is restricted to a specified depth by a penetration-restricting feature that forms part of the package.

United States Patent Application No. 2008/0078382 A1 to LeMahieu et al. describes systems and methods for delivery of a drug to the respiratory system of a patient in a stream of purified air are provided. In particular, the drugs are delivered to the respiratory system of the patient at a positive air pressure relative to atmospheric pressure. With the systems and methods of the present disclosure, medication available in a variety of forms is introduced in a controlled fashion into the air stream in aerosol, nebulized, or vaporized form.

United States Patent Application No. 2008/0066741 A1 to LeMahieu et al. describes systems and methods for delivery of a drug to the respiratory system of a patient, where the drug is supplied in purified air at a positive pressure relative to atmospheric pressure. With the systems and methods of the present disclosure, medication available in a variety of forms is introduced in a controlled fashion into the purified air stream in aerosol, nebulized, or vaporized form.

United States Patent Application No. 2008/0066739 A1 to LeMahieu et al. describes systems and methods for delivery of a drug to the respiratory system of a patient where the drug is supplied at a positive pressure relative to atmospheric pressure. In particular, the drugs are delivered to the respiratory system of a patient who is capable of unassisted breathing. With the systems and methods of the present disclosure, medication available in a variety of forms is introduced in a controlled fashion into the air stream in aerosol, nebulized, or vaporized form.

United States Patent Application No. 2008/0029086 A1 to Harlan, et al. describes a nasal passage washing device includes a pliable body including an open top; and an applicator cap removably attached to the pliable body to cover and uncover the open top. The applicator cap includes an applicator tip having a substantially frustoconical configuration sized and shaped for receipt at least partially within a nostril of a user for sealing engagement therewith, the applicator tip including a hole to transfer washing solution there through, a washing solution transfer tube in communication with the hole of the applicator tip and a bottom of an inside of the pliable body to transfer washing solution from the bottom of the inside of the pliable body to the hole of the applicator tip, and a one-way air valve that only allows air flow into the pliable body through the one-way air valve and does not allow air flow and washing solution flow out of the pliable body through the one-way air valve.

United States Patent Application No. 2006/0172017 A1 to Rasor et al. describes an apparatus and methods to deliver vasoconstrictive agents simultaneously with capnic gases. The capnic gases can enhance the effectiveness of the vasoconstrictive agent, lower the dosage of drug or concentration of agent necessary to achieve a therapeutic result, or both. Exemplary capnic gases include carbon dioxide, nitric oxide, nitrous oxide, and dilute acid gases.

United States Patent Application No. 2004/0009126 A1 to Pilkiewicz et al. describes an inhalation system comprising an anti-infective agent in particle form, the anti-infective agent being directed toward prevention and treatment of intracellular infection, and an inhalation device, and a method of use of the system.

United States Patent Application No. 2002/0174864 A1 to Alchas describes a nasal delivery device for delivering substances such as liquid drugs, vaccines and the like to a nasal passage. The nasal delivery device preferably comprises a drug container such as syringe and a separable spray nozzle. The spray nozzle includes a rigid plastic cap having a spray aperture at a distal end of the nozzle for delivering the liquid substance to the nasal passage. Attachment means is provided for attaching the spray nozzle to the syringe at the time of the delivery of the liquid substance to the nasal passage. The nozzle defines a conduit that allows fluid communication from the syringe to the spray aperture. The nozzle includes an internal valve between the spray aperture and the syringe for allowing only pressurized liquid substance to flow through the conduit and the aperture so that a mist or spray is delivered through the spray aperture.

United States Patent Application No. 2002/0040205 A1 to Rasor et al. describes methods and devices for transcutaneous and transmucosal application of carbon dioxide in the form of gas and in the form of a capnic solution (such as carbonated water) for the relief of pain, including musculoskeletal disorders, neuralgias, rhinitis and other ailments. Gaseous carbon is applied to the skin for at least three minutes, and the capnic solution may be held on the skin for at least three minutes, which provides relief of symptoms. The capnic solution may be sprayed onto mucous membranes such as the nose for relief of symptoms such as allergic rhinitis.

Casale, et al., "Nasal Carbon Dioxide for the Symptomatic Treatment of Perennial Allergic Rhinitis," Ann Allergy Asthma Immunol., October 2011, pp. 364-370, examines the safety and efficacy of nasal carbon dioxide on the symptoms of perennial allergic rhinitis.

Baroody et al., "The Effect of Intranasal Carbon Dioxide on the Acute Response to Nasal Challenge with Allergen," Allergy Asthma Proc., May-June 2011, pp. 206-212 describes a study in which intranasal carbon dioxide (CO(2)) was shown to reduce symptoms of seasonal allergic rhinitis (SAR). This study was designed to evaluate the effect of CO(2) on nasal allergen challenge. We conducted a randomized, controlled, crossover trial in 12 subjects with SAR outside their pollen season. Thirty minutes after a 20-second exposure to CO(2) or no exposure, subjects underwent a unilateral, localized, nasal allergen challenge. Filter paper disks were placed on the nasal septum to deliver a sham challenge followed by 2 increasing doses of either grass or ragweed allergen. Secretions were collected from both sides of the septum to evaluate the nasonasal reflex and were assayed for histamine. Nasal and eye symptoms were recorded. The primary outcome measure was the contralateral, reflex, secretory response to allergen as measured by secretion weights. Secondary outcome measures included ipsilateral nasal secretion weights, nasal and eye symptoms, levels of histamine in nasal secretions, and eosinophils in nasal scrapings. Subjects reported a transient burning sensation during exposure to CO(2). Compared with no treatment, active treatment resulted in a significant reduction in sneezes ($p=0.05$), contralateral secretion weights ($p=0.04$), and bilateral runny nose symptoms ($p=0.01$). Ipsilateral secretion weights were numerically reduced. Histamine levels in ipsilateral nasal secretions increased significantly when the subjects received sham treatment but did not increase after pretreatment with CO(2). Treatment with nasal CO(2) resulted in partial reduction of the acute response to allergen challenge. Reflex responses were reduced, supporting an effect on neuronal mechanisms, which predict usefulness in the treatment of allergic rhinitis.

Pagani et al., "Carbon Dioxide-Enriched Water Inhalation in Patients With Allergic Rhinitis and its Relationship with Nasal Fluid Cytokine/Chemokine Release," Arch Med Res, May 2011, pp. 329-333 investigates a possible in vivo effect of carbon dioxide-enriched water inhalation in patients with allergic rhinitis.

Casale, Romero, and Spierings, "Intranasal Noninhaled Carbon Dioxide for the Symptomatic Treatment of Seasonal Allergic Rhinitis," J Allergy Clin Immunol., January 2008, pp. 105-109, studies whether noninhaled intranasal CO2 would be effective in the treatment of seasonal allergic rhinitis.

Notwithstanding the prior art, the present invention is neither taught nor rendered obvious thereby.

SUMMARY OF INVENTION

The present invention is directed to a method of treating lower body cavity ailments via application of one or more dosages of a treatment to an area of the patient in need of treatment, wherein the dosage includes dissolved carbon dioxide gas, dissolved in a saline solution, with some carbonic acid, and with or without additional active additives. Thus, in some preferred embodiments, the present invention includes methods for treating or preventing lower body cavity ailments in a patient in need thereof. The method comprises: directing (spraying) a therapeutic, dosage to at least one area of said patient selected from the group consisting of oral cavity, eye, ear canal, skin care area and foot care area, through a flow regulating device having a flow channel, said dosage including: (a) a saline fluid, (b) dissolved carbon dioxide gas, (c) carbonic acid as an active antibacterial component, and (d) at least one additional active component, wherein the therapeutic, dosage is delivered at a flow rate through said flow channel of the combined saline fluid, carbon dioxide, carbonic acid and said at least one additional active component, does not exceed 25.0 cc per second, and the carbon dioxide therein does not exceed 1.0% by weight based on the entire weight of the dosage. In other preferred embodiments, present invention method for treating non-nasal ailments in a patient in need thereof, said method comprising: directing a therapeutic, dosage to at least one area of said patient selected from the group consisting of oral cavity, eye, ear canal, skin care area and foot care area, through a flow regulating device having a flow channel, said dosage including: (a) a saline fluid, (b) dissolved carbon dioxide gas, and (c) carbonic acid as an active antibacterial component, wherein the therapeutic, non-inhaled dosage is delivered at a flow rate through said flow channel of the combined saline fluid and gaseous carbon dioxide does not exceed 25.0 cc per second and the carbon dioxide therein does not exceed 1.0% by weight based on the entire weight of the dosage.

In some preferred embodiments, with or without the additional active additive(s), the ailment is a vaginal ailment. These treatments include infection reduction/elimination, douches, flushes, cleansing and pre-surgical, surgical and post-surgical treatments. In some other preferred embodiments, with or without the additional active additive(s), the ailment is an intestinal ailment. These intestinal treatments include infection reduction/elimination, enemas, flushes, cleansing and pre-surgical, surgical and post-surgical treatments. In some other preferred embodiments, with or without the additional active additive(s), the ailment is a urinary ailment. These urinary tract treatments include infection reduction/elimination, flushes, cleansing and pre-surgical, surgical and post-surgical treatments. In some embodiments, a tube extension is used to create more user friendly and/or doctor friendly devices. Thus, tube extensions may be used as tubes for inserting and treating or for hosing with treatment dosages. These extension tubes have distal end (away from the container) outlets that may be simply the ends of the tubes, or may include body cavity inserts, such as the rigid tubing used by urologists to dilate/treat a urinary tract. In other embodiments, the tube extension may include a bulbous portion and a stop flange that basically functions as an anus plug such as would be advantageous for delivery of enema dosages.

In some other preferred embodiments of the present invention, with or without the additional active additive(s), the flow regulating device is selected from the group consisting of a single dose dispenser with a pressure control valve for released flow regulation and a multiple dose dispenser with a pressure control valve for released flow regulation, and the multiple dose dispenser further includes a dosage amount control mechanism and activator to limit dosage release amount for each activation.

In some other preferred embodiments, with or without the additional active additive(s), the duration of spraying each dosage is ½ to 20 seconds. In some other preferred embodiments, with or without the additional active additive(s), the dose is repeated from 1 to 10 times.

In some other preferred embodiments, with or without the additional active additive(s), the flow rate through the flow channel of the combined saline fluid, carbon dioxide, carbonic acid and with or without at least one additional active component, is in the range of 0.2 cc per second to 10.0 cc per second and the carbon dioxide therein is in the range of 0.05% to 1.0% by weight based on the entire weight of the dosage. In some other preferred embodiments, with or without the additional active additive(s), the flow rate through the flow channel of the combined saline fluid, carbon dioxide, carbonic acid with or without at least one additional active component, is in the range of 0.4 cc per second to 4.0 cc per second and the carbon dioxide therein is in the range of 0.2% to 0.8% by weight based on the entire weight of the dosage. In yet some other preferred embodiments, with or without the additional active additive(s), the flow rate through the flow channel of the combined saline fluid, carbon dioxide, carbonic acid and the at least one additional active component is in the range of 0.4 cc per second to 2 cc per second and the carbon dioxide therein is in the range of 0.2% to 0.6% by weight based on the entire weight of the dosage.

Other preferred embodiments of the present invention include a device. Specifically, it is a releasable lower body cavity treatment delivery device for treating at least one of the lower cavity areas of a patient mentioned above, with a mixture containing carbon dioxide and saline. This present invention device comprises: a) a main housing having a proximal and a distal end and having a hollow central area containing a releasable lower body cavity treatment dosage that includes a saline fluid and a gaseous carbon dioxide, with or without the additional active additive(s), wherein the gaseous carbon dioxide is dissolved in the saline fluid; b) a dosage dispenser head located at the distal end of the main housing, the dosage dispenser head having at least one flow channel for movement of the dosage from the main housing through the dosage dispenser head and externally of the dosage dispenser head; c) a dosage release control component located between the main housing and the dosage dispenser head adapted to permit flow of the dosage comprising the saline fluid and the gaseous carbon dioxide from the main housing and through the dosage dispenser head in response to increased pressure against the dosage release control component wherein the permitted flow has controlled release at a flow rate that does not exceed 25 cubic centimeters per second and the carbon dioxide therein does not exceed 1.0% by weight, based on the total weight of the dosage, and wherein the flow rate is a total flow rate of the dosage; d) a pressure-changing moveable component located on the main housing, wherein, when the dosage dispenser head of the device is placed in an area to be treated and the pressure-changing moveable component is activated by movement toward the dosage, the dosage is at least partially forced through the dosage release control component at the permitted flow rate and through the dosage dispenser head for application of the dosage to the area to be treated.

In some preferred embodiments of the present invention treatment delivery device, the dosage release control component is selected from the group consisting of a frangible member, a puncturable member and a one-way valve. In some preferred embodiments of the present invention non-nasal treatment delivery device, the main housing is an open ended tube with the dosage release control component and the dosage dispenser head is located at the distal end of the main housing and the pressure-changing moveable component is located at the proximal end of the main housing. In some preferred embodiments of the present invention device, the pressure-changing moveable component is a push-up piston. In some preferred embodiments of the present invention non-nasal treatment delivery device, the main housing is a tube having an open distal end and a closed proximal end, with the dosage release control component and the dosage dispenser head being located at the distal end of the main housing, and at least a portion of the tube is flexible and constitutes the pressure-changing moveable component comprising a push-up piston. As mentioned, the devices of the present invention may also include extension tubes, insertion end components and bulbous ends with flanges.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings:

FIG. 2 is a block diagram showing ailments treated by various embodiments of the present invention carbon dioxide, carbonic acid and saline lower body cavity delivery devices;

FIG. 3 is a block diagram showing durations for therapeutic lower body cavity dosage in some preferred embodiments of the present invention carbon dioxide, carbonic acid and saline lower body cavity delivery devices;

FIG. 5 is a block diagram showing flow rates in some preferred embodiments of the present invention device carbon dioxide, carbonic acid and saline lower body cavity delivery methods and treatments;

FIG. 6 is a block diagram showing the percentage of carbon dioxide present in the dosages, based on the total weight of the dosages, in some preferred embodiments of the present invention device carbon dioxide, carbonic acid and saline lower body cavity delivery methods and treatments;

FIG. 8 illustrates a front partially cut view of one embodiment of a present invention treatment delivery device with a pressure release mechanism;

FIG. 9 illustrates a view of one embodiment of a present invention treatment delivery device that is a squeeze to release device;

FIG. 10 shows a front partially cut view of a present invention treatment delivery device with a piercing channel, with the device being held in a hand using two fingers and a thumb to activate release of the medicinal treatment;

FIGS. 11, 12 and 13 illustrate front partially cut views of one embodiment of a present invention lower body cavity treatment delivery device with a frangible internal medicine capsule that may be used for a monodose or multidose using replacement cartridges. The three Figures show the device in different stages of use;

DETAILED DESCRIPTION OF THE EMBODIMENTS

Figure 1:
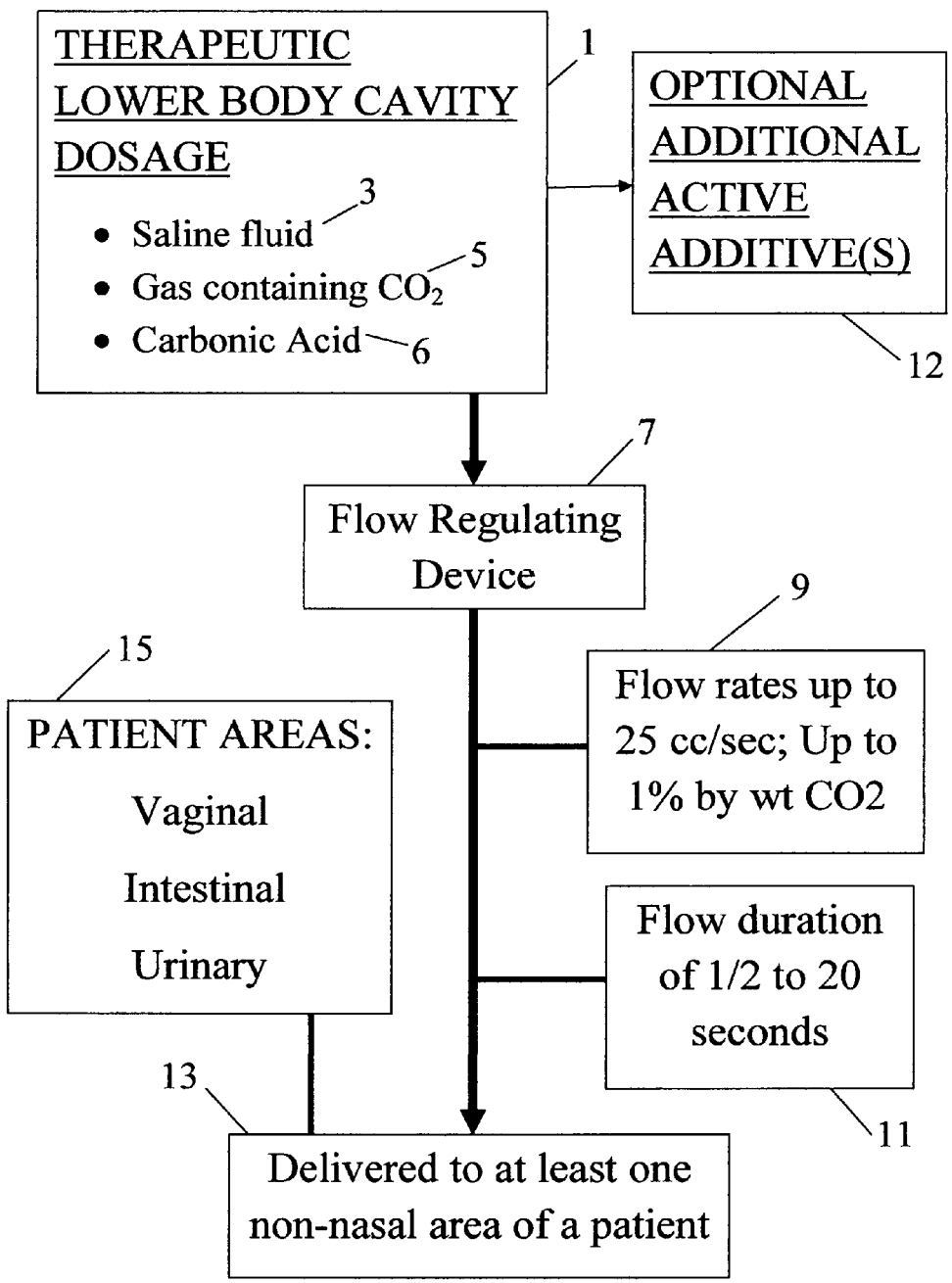
FIG. 1 is a block diagram of an embodiment of the present invention device carbon dioxide, carbonic acid and saline lower body cavity delivery methods and treatments.

Saline" and "saline solution" as used herein mean water containing salt. Water may be sea water or not sea water. For human use, both sea water and fresh water are purified before consumption. Salt is sodium chloride. Saline solutions are used in a wide variety of medical applications. For example, "normal saline" and "isotonic saline" are the commonly used terms for a solution of 0.90% w/v of sodium chloride (NaCl). Normal saline is frequently used in intravenous drips for patients unable to take fluids orally to prevent dehydration. Normal saline is also used as a nasal cleanser and to flush wounds and skin abrasions. Another application of saline solution is as a rinse for contact lenses. Saline is also used as a rinse and treats symptoms whereas the present invention methods and devices kill off all or a portion of many causes of these ailments and thus are different and act very differently from saline without the carbon dioxide/carbonic acid as in the present invention.

Saline solution also is frequently used in some non-nasal washes to treat some of the symptoms of infections or other ailments adversely affecting the various areas of the patient's cavities and body areas. By irrigating ailing body areas and cavities with saline, inflammation can be reduced. Also, more concentrated ("hypertonic") solutions of NaCl, can have therapeutic uses. For example, 7% NaCl/water solutions are considered mucoactive agents and as such are used to hydrate thick secretions (mucous) in order to make it easier to cough up and out (expectorate).

Another chemical substance useful in medical treatments is carbon dioxide. One example is the use of diluted carbon dioxide by inhalation for treating symptoms related to headaches, allergies, asthma, nervous disorders, and other common ailments, which was demonstrated in the 1940s and 1950s. Another example is the use of high-concentration, non-inhaled carbon dioxide, delivered to the nasal passages locally. This type of treatment may provide fast relief without the adverse side effects of systemic drugs that are inhaled, ingested, or injected.

Carbon dioxide, when dissolved in water, and, as in the present invention, when dissolved in saline, will dissolve so as to include dissolved gas, as well as some in situ formed carbonic acid and some possible other ionic constituents. This formed carbonic acid functions as a separate active so as to aid in the reduction of the pH of the dosage and to thus function as an antibacterial agent and with efficacy in disrupting biofilms. In the present invention, carbonic acid is formed when the carbon dioxide is dissolved, and in some embodiments no additional carbonic acid is added, whereas in other embodiments, additional carbonic acid is added to the dosage. In those embodiments wherein only the in situ formed carbonic acid is present, the amount of carbonic acid depends upon temperature, pressure, pH and carbon dioxide dissolved-then it is the amount that forms for that stoichiometry at equilibrium. If additional carbonic acid is added, then equilibrium shifts and the amount of carbonic acid in the dosage is increased above in situ formation equilibrium. About 0.01% up to and including 0.4% by weight of carbonic acid based on the total weight of the dosage is the desired range, although more or less could be included. Preferred range of carbonic acid is 0.01% to 0.1%, and most preferred is 0.02% to 0.08% by weight based on the total weight of the dosage.

As stated, the saline solutions further include carbonic acid, which acts to lower pH and inhibit or destroy bacteria. In some embodiments, the dosage also contains one or more additional active components (flavorings, minerals, vitamins, medicines, or other physiologically or psychologically beneficial to the user (patient or consumer)). Specified flow rates of the present invention methods and delivery devices for the dissolved carbon dioxide, carbonic acid and saline dosage, with and without other active additives, are specified for treating lower body cavity ailments in a patient in need thereof. "Treatment" and "treating" as used herein should be taken broadly to include preventative treatments, curative treatments, symptom reducing treatments, pain relieving, healing and any other treatments given by the medical and natural medicine communities.

The present invention involves combining the beneficial therapeutic effects of saline treatment and carbon dioxide/carbonic acid treatment that, relative to either component, is an improved and synergistic therapy with unexpected favorable consequences. In this way, the beneficial effects of the saline are combined with the beneficial effects of carbon dioxide therapy. Further, the saline moisturizes the treated areas and acts as a base host for the carbon dioxide/carbonic acid as they act on the areas in need of treatment to deliver, in addition to the benefits of saline, lower pH and active attack on various bacteria and infection, as well as micro-stimulation of nerves and of blood vessels. (It is hypothesized that at least some of the carbon dioxide is adsorbed by the saline.) In addition, the saline reduces any slight burning that might otherwise be felt from the carbon dioxide. In this way, the benefits of saline treatment are supplemented by the benefits of carbon dioxide treatment, and the benefits of carbon dioxide treatment are supplemented by the benefits of saline treatment. This combination of utilizing the saline to perform at least moisturizing and other beneficial affects while carrying and enhancing the delivery of the carbon dioxide is an unexpected synergistic result thereof. By the methods and devices of the present invention unexpected results are obtained. Specifically, much smaller dosages of carbon dioxide (orders of magnitude less) are used to obtain better results than gaseous carbon dioxide, and the kill rate as shown by biofilm independent testing is evident versus saline, wherein no kill rate is observed. These and other benefits are shown below.

In addition to the benefits listed above, the present invention device using carbon dioxide and saline non-nasal delivery methods and treatments have other synergistic benefits that are not available from either saline treatment or carbon dioxide treatment alone. For example, the presence of dissolved carbon dioxide in the saline solution means that the solution will be carbonated; the effervescent effect of the carbon dioxide helps the saline solution to mix more energetically against the areas of the treatment. This improved mixing allows the saline treatment to be more effective. Another potential advantage of combining carbon dioxide and saline treatments is that in some embodiments, with sufficient pressure and a proper nozzle, the carbon dioxide can act as a carrier gas for the saline, allowing the saline solution to be aerosolized. This means that a better, well distributed delivery occurs.

To summarize the advantages and benefits of the present invention, the combination of controlled delivery carbon dioxide and saline provides the following: it cleanses the treated area, removing allergens, irritants and particulates that cause inflammation and congestion; its special formula shields treated areas from viruses; it soothes and moisturizes; its unique buffering system neutralizes irritants such as oxidative free radicals and endogenous cytotoxins which cause inflammation and damage; it enhances mucous and other body debis clearance and flow by, for example, reducing mucus viscosity; its superior safety profile gives it broader application than corticosteroids and decongestants and can be used safely in children 6 months of age and adults, even with co-morbidities such as diabetes, hypertension, suppressed immune systems and pregnant and nursing females; and its exceptional safety profile allows for flexible dosing. In addition, it will inhibit and even destroy the causes of ailments, unlike other non-drug treatments that only affect symptoms.

Vaginal, rectal and urinary wounds are one type of treatment that may be treated with the present invention. Such wounds are unlike typical wounds in that they may be slower to heal, making treatment with conventional medications an uphill process. Among several different alternative therapies, carbonated saline/seawater is an effective non-drug choice because it provides comparatively rapid wound healing versus regular saline/seawater. The application of carbonated saline/seawater to such wounds has only recently been recognized because it can combat many microorganisms via its lower pH due to carbonic acid, the intrinsic ability of carbon dioxide to act as a natural antioxidant which blunts the formation of inflammatory mediators that exacerbate local inflammation (and pain) that lead to increased healing times. Longer healing times are also associated with increased risk of wound infection and general treatment complications. Lastly, it has been documented that carbon dioxide enriched water increases microcirculation via capillary dilation thus providing enhanced blood flow to tissue reducing overall tissue damage, reduced formation of necrotic tissue and better outcomes in recovery. Such wound treatments would include accidentally induced, ailment modality induced and surgically induced wounds.

Various present invention formulations were prepared for treatments of lower body cavity areas: vaginal, urinary and intestinal areas, in accordance with Table 1 and Table 2, Below:

TABLE 1

Present Invention Sample Carbon Dioxide, Carbonic Acid, Saline Formulations with Purified Water and Salt, less than 0.1% Carbonic Acid, and with and without Other Actives

| Formula (all % wt/wt) | Liquid | Salt | Carbon Dioxide | Active Additive |
|---|---|---|---|---|
| W-1 (Isotonic A) | Purif. Water 98.8% | 0.9% | 0.3% | 0% |
| W-2 (Isotonic B) | Purif. Water 98.5% | 0.9% | 0.6% | 0% |
| W-3 (Isotonic C) | Purif. Water 98.4% | 0.9% | 0.7% | 0% |
| W-4 (Isotonic D) | Purif. Water 98.6% | 0.9% | 0.3% | <0.2% Mg, Zn |
| W-5 (Isotonic E) | Purif. Water 96.5% | 0.9% | 0.6% | 2% moisturizer |
| W-6 (Isotonic F) | Purif. Water 97.0% | 0.9% | 0.6% | 1.5% decongestant |
| W-7 (Isotonic G) | Purif. Water 98.8% | 0.9% | 0.5% | <0.2% micronutrients |
| W-8 (Isotonic H) | Purif. Water 97.5% | 0.9% | 0.6% | 1% humectant |
| W-9 (Isotonic I) | Purif. Water 97.0% | 0.9% | 0.6% | 1.5% decongestant |
| W-10 (Isotonic J) | Purif. Water 98.4% | 0.9% | 0.3% | 2% to <0.1% choice* |
| W-11 (Hypotonic A) | Purif. Water 96.8+% | 0.8% | 0.3% | 2% to <0.1% choice* |
| W-12 (Hypotonic B) | Purif. Water 96.7% | 0.7% | 0.6% | 2% moisturizer |
| W-13 (Hypotonic C) | Purif. Water 97.3% | 0.6% | 0.6% | 1.5% antihistamine |
| W-14 (Hypotonic D) | Purif. Water 98.6% | 0.8% | 0.3% | <0.2% micronutrients |
| W-15 (Hypertonic A) | Purif. Water 97.9% | 1.8% | 0.3% | 2% hydrogenperoxide |
| W-16 (Hypertonic B) | Purif. Water 97.0% | 2.4% | 0.6% | 0% |
| W-17 (Hypertonic C) | Purif. Water 97.5% | 1.8% | 0.7% | 0% |
| W-18 (Hypertonic D) | Purif. Water 97.4% | 2.1% | 0.3% | <0.2% Mg, Zn |
| W-19 (Hypertonic E) | Purif. Water 95.5% | 1.9% | 0.6% | 2% moisturizer |
| W-20 (Hypertonic F) | Purif. Water 96.1% | 1.8% | 0.6% | 1.5% decongestant |
| W-21 (Hypertonic G) | Purif. Water 98.0% | 1.3% | 0.5% | <0.2% micronutrients |
| W-22 (Hypertonic H) | Purif. Water 96.5% | 1.9% | 0.6% | 1% humectant |
| W-23 (Hypertonic I) | Purif. Water 9.4% | 1.5% | 0.6% | 1.5% decongestant |
| W-24 (Hypertonic J) | Purif. Water 95.9+% | 1.8% | 0.3% | 2% to <0.1% choice* |

TABLE 2

Present Invention Sample Carbon Dioxide, Carbonic Acid (same as Table 1), Saline Formulations with Purified Sea Water, with and without Other Active Additives

| Formula (all % wt/wt) | Liquid | Salt | Carbon Dioxide | Active Additive |
|---|---|---|---|---|
| S-1 (Isotonic K) | Purif. SeaWtr 98.8% | 0.9% | 0.3% | 0% |
| S-2 (Isotonic L) | Purif. SeaWtr 98.5% | 0.9% | 0.6% | 0% |
| S-3 (Isotonic M) | Purif. SeaWtr 98.4% | 0.9% | 0.7% | 0% |
| S-4 (Isotonic N) | Purif. SeaWtr 98.6% | 0.9% | 0.3% | <0.2% Mg, Zn |
| S-5 (Isotonic O) | Purif. SeaWtr 96.5% | 0.9% | 0.6% | 2% moisturizer |
| S-6 (Isotonic P) | Purif. SeaWtr 97.6% | 0.9% | 0.6% | 0.9% decongestant |
| S-7 (Isotonic Q) | Purif. SeaWtr 98.8% | 0.9% | 0.5% | <0.2% micronutrients |
| S-8 (Isotonic R) | Purif. SeaWtr 97.5% | 0.9% | 0.6% | 1% humectants |
| S-9 (Isotonic S) | Prnif. SeaWtr 97.0% | 0.9% | 0.6% | 1.5% decongestant |
| S-10 (Isotonic T) | Purif. SeaWtr 98.4% | 0.9% | 0.3% | 2% to <0.1% choice* |
| S-11 (Hypotonic E) | Purif. SeaWtr 96.8+% | 0.8% | 0.3% | 2% to <0.1% choice* |
| S-12 (Hypotonic F) | Purif. SeaWtr 96.7% | 0.7% | 0.6% | 2% moisturizer |
| S-13 (Hypotonic G) | Purif. SeaWtr 97.3% | 0.6% | 0.6% | 1.5% decongestant |
| S-14 (Hypotonic H) | Purif. SeaWtr 98.6% | 0.8% | 0.3% | <0.2% micronutrients |
| S-15 (Hypertonic K) | Purif. SeaWtr 97.0% | 2.4% | 0.6% | 0% |
| S-16 (Hypertonic L) | Purif. SeaWtr 97.5% | 1.8% | 0.7% | 0% |
| S-17 (Hypertonic M) | Purif. SeaWtr 97.4% | 2.1% | 0.3% | <0.2% Mg, Zn |
| S-18 (Hypertonic N) | Purif. SeaWtr 95.5% | 1.9% | 0.6% | 2% moisturizer |
| S-19 (Hypertonic O) | Purif. SeaWtr 96.6% | 1.8% | 0.6% | 1.0% decongestant |
| S-20 (Hypertonic P) | Purif. SeaWtr 98.0% | 1.3% | 0.5% | <0.2% micronutrients |
| S-21 (Hypertonic Q) | Purif. SeaWtr 96.5% | 1.9% | 0.6% | 1% humectants |
| S-22 (Hypertonic R) | Purif. SeaWtr 9.4% | 1.5% | 0.6% | 1.5% decongestant |
| S-23 (Hypertonic S) | Purif. SeaWtr 95.9+% | 1.8% | 0.3% | 2% to <0.1% choice* |

*Choice can be any one or more additional active additives, including, but not limited to mineral supplements, vitamin supplements, micronutrients such as are found in sea water or otherwise added, humectants, decongestants and others. Choice may include one or more of these or as otherwise set forth in the above tables, as well as Table 3, below.

While various ranges of water, salt and carbon dioxide, and optional additives are shown in Tables 1 and 2, it must be noted that carbonic acid is also included at equilibrium values with the dissolved carbon dioxide, and is thus less than 0.1%. Also, to create additional examples, all of the above formulations with the equilibrium carbonic acid amounts are repeated and an additional 0.2% of carbonic acid is added to create additional, lower pH sample examples. It should be further noted that all formulations in the Tables and stated herein are merely exemplary and not intended as limiting. For example, supersaturated carbon dioxide in saline could be included in the above and the percentage of carbon dioxide would be greater than as shown. Likewise, different salt concentrations could be used. Also, while the preferred salt is sodium chloride, other human-acceptable and functional salts may partially or fully replace the sodium chloride. Further, active additives could be significantly higher in content, such as analgesics or vitamins that have optimal efficacy at 5% could be included, wherein water/salt content would be reduced accordingly.

In the present invention dosage of the saline and carbon dioxide and carbonic acid, with or without at least one additional active component, the carbon dioxide therein does not exceed 1.0% by weight based on the entire weight of the dosage. In some embodiments of the present invention treatment, the carbon dioxide therein is in the range of 0.05% to 1.0% by weight based on the entire weight of the dosage. In some preferred embodiments of the present invention, the carbon dioxide therein is in the range of 0.2% to 0.8% by weight based on the entire weight of the dosage. In some more preferred embodiments, the carbon dioxide therein is in the range of 0.2% to 0.6% by weight based on the entire weight of the dosage. In most cases, when one or more additional actives are added, the water content is reduced by the additional weight of the one or more active additives. However, any combination of all constituents within the above and below stated ranges may be used, with the balance being water (and/or sea water).

TABLE 3

Other Possible Active Additives In addition to Carbonic Acid

Antihistamines
Decongestants
Suppressants
Tissue Conditioners
Tissue Protectants
Antioxidants
Sugar Alcohols
Fatty Acids
Microminerals
Micronutrients
Buffers
Anti-biotics
Bacteriostatic agents
Bacterialcidal agents
Antivirals
Mucolytic agents
Expectorants
Anesthetic agents
Polymers
Surfactants
Preservatives
Chelating Agents
Agents that increase bodily fluid flow
Agents that maintain bodily fluid flow
Agents that reduce bodily fluid flow
Healing Agents
Non Steroidal Anti-inflammatory agents
Steroids
Flavoring Agents
Fragrances
Osmotic Agents
Lubricants
Moisturizers
Sweeteners
Immunological Therapeutic Agents
RNS Scavengers TABLE 3-continued Other Possible Active Additives
In addition to Carbonic Acid ROS Scavengers
Vasoconstrictors
Stimulants (Caffeine)
Chemotherapeutics
Natural Extracts
Botanicals
Homeopathic medicines
Traditional Chinese medicines
Herbals
Ayurvedic medicine
counter-irritants
Hormones
Growth Factors
Hyaluronic And Salts
Cellular Metabolites
Sedatives
Sleep Inducing Agents
Antidepressants
Anti Anxiolytics
Psychotropics
Debriding Agents
Enzymes
Oxygen Generators
Reducing Agents
Chlorinating Agents
Analgesics
Alertness Aids
Resuscitation Agents
Vitamins The above Table 3 illustrates numerous active additives that may be included in the saline/carbon dioxide solutions of the present invention. Many specifics can now be realized from Table 3 without enumerating thousands upon thousands of potential additives.

Referring now in detail to the drawings wherein like reference numerals designate corresponding parts throughout the several views, various embodiments of the present invention are shown.

FIG. 1 is a block diagram of an embodiment of the present invention device and carbon dioxide, carbonic acid and saline lower body cavity delivery methods and treatments. FIG. 1 illustrates a therapeutic dosage 1 containing saline fluid 3, a gas containing carbon dioxide 5 and carbonic acid 6. The saline fluid 3 contains water and at least one salt. In some preferred embodiments of the present invention, the salt is sodium chloride. In other embodiments of the present invention, other salts may be used, but it is important that any salt used in the saline fluid 3 must be safe for human use. In some preferred embodiments of the present invention, the concentration of salt in the saline fluid is approximately isotonic with the salt concentration of bodily fluids. In other preferred embodiments, the concentration of salt in the saline fluid is less than the concentration of salt in bodily fluids, i.e., is hypotonic (less than human bodily fluid salt content). In still other preferred embodiments, the concentration of salt in the saline fluid is hypertonic, meaning that it has a salt concentration higher than that of bodily fluids. In still other preferred embodiments, the saline solution is saturated with salt.

The gas 5 contains some portion of carbon dioxide, and is preferably all carbon dioxide dissolved into the saline. As it dissolves in the saline, carbonic acid 6 is formed in situ. Additional carbonic acid may optionally be added to lower pH further. Human tolerable acid pH levels are desirable and may range in the area of 3.5 to 4.6. When the gas 5 containing carbon dioxide is added to the saline fluid 3, the saline fluid 3 becomes carbonated. If the therapeutic dosage 1 containing saline fluid 3, the gas 5 that is now dissolved, and the carbonic acid 6, is kept under pressure, the pressure can later be released (for example by opening a valve, e.g., by pushing or pressing), which causes some of the carbon dioxide to bubble out with the solution for a well dispersed mixture of the gas and liquid. This sudden release of carbon dioxide in the saline creates effervescence in the therapeutic dosage.

The therapeutic dosage travels through a flow-regulating device 7. In preferred embodiments, the flow-regulating device 7 controls the flow rate 9 of the therapeutic dosage 1 at a rate that is safe and comfortable for the patient and the area treated. For example, eye, ear and oral applications may have slower flow rates than skin treatments or foot treatments. Wound care may be faster flows to flush out unwanted debris in an accidental laceration, for example. In the embodiment shown in FIG. 1, the flow rate 9 of the therapeutic dosage that contains the combined saline fluid, dissolved carbon dioxide, carbonic acid and optional at least one additional active component 12 (through an exit flow channel) does not exceed 25 cubic centimeter per second (cc/sec) and the carbon dioxide therein does not exceed 1.0% by weight based on the entire weight of the dosage. In some preferred embodiments, this flow rate is in the range of 0.2 cc per second to 10.0 cc per second for the combined saline fluid, dissolved gas carbon dioxide, carbonic acid and optional at least one additional active component, and the carbon dioxide therein is in the range of 0.05% to 1.0% by weight based on the entire weight of the dosage. In some embodiments, this flow rate is in the range of 0.4 cc per second to 4.0 cc per second for the combined saline fluid, dissolved gas carbon dioxide, carbonic acid and optional at least one additional active component. The carbon dioxide therein is in the range of 0.2% to 0.8% by weight based on the entire weight of the dosage. In some preferred embodiments, this flow rate is in the range of 0.4 cc per second to 2 cc per second for the combined saline fluid, dissolved gas carbon dioxide, carbonic acid and optional at least one additional active component. The carbon dioxide therein is in the range of 0.2% to 0.6% by weight based on the entire weight of the dosage. Excellent results have been obtained with present invention overall flow rates of about ½ to 5 cc/sec, for eye, ear and oral cavity applications, although, as mentioned above, higher flow rates may be used.

Note that FIG. 1 also clearly shows optional additional active additives, block 12, and may be any, in any combination as described elsewhere herein.

The therapeutic non-inhaled dosage 1 has a flow duration 11. The flow duration 11 is the length of time during which the therapeutic non-inhaled dosage flows through the flow regulating device into the area of a patient being treated. In the embodiment shown in FIG. 1, the flow duration 11 is shown as lasting between ½ and 20 seconds. In preferred embodiments of the present invention, the flow duration is adjustable to any value based on the time the user depresses or pushes on the valve activator or other release mechanism. Excellent results have been obtained with single shots and multiple shots to the eye of ½ to 3 seconds.

After the therapeutic non-inhaled dosage 1 leaves the flow regulating device 7, it enters at least one non-nasal area of a patient 13. The specific general areas to which this dosage is applied, are shown in block 15. The therapeutic non-inhaled dosage 1 is adsorbed by the treated area and may at least partially subsequently absorbed by the body. This adsorption and subsequent absorption can have a beneficial effect on many ailments, some of which are shown in FIG. 2. The effervescent effect of the gas 5 containing carbon dioxide causes better contact between the salt and carbonic acid in the saline solution 3 and the bodily area being treated. There appears to be multiple synergistic benefits: the gas helps in the creation of more of a mist than when there is no gas, distribution is broader and gentler; the transport phenomena are enhanced—the gas holds the liquid up and there is less dripping, likewise, the gas increases the surface area of the liquid, and the liquid better holds the gas in place in the area being treated.

In the present invention solutions, when the concentration of salt in the saline solution 3 is greater than isotonic (particularly if salts other than sodium chloride are used), it is desirable to limit the patient's ingestion of the salts. Therefore, when applied to the oral cavity, it is preferred to request that the user rinse and expel the hypertonic solution. However, there is no significant harm in ingestion of hypertonic solutions, but it is a salty solution to swallow.

Turning now to FIG. 2, a block diagram, block 20, shows some of the medical conditions (ailments) that can be treated using the present invention device with carbon dioxide and saline delivery methods and treatments, with or without different additional actives. In some embodiments of the present invention, the carbon dioxide and saline delivery methods and treatments treat vaginal area ailments 17. This could be in, around, outside or beyond the vagina. In other embodiments, the present invention is used for intestinal area ailments 19. In still other embodiments, the present invention is used urinary tract ailments 21. In many of these embodiments of the present invention, the present invention purposes include, but are not limited to, flushes, cleansings, douches, enemas, anti-infections and medicine deliveries. It is important to recognize that in some embodiments of the present invention carbon dioxide and saline delivery methods and treatments, multiple conditions can be treated simultaneously. For example, a patient may be suffering from both a scratched and infected vaginal cavity simultaneously; the present invention methods and devices can alleviate both conditions at the same time. The present invention can treat any ailment shown in FIG. 2 or any combination of those ailments. It should also be recognized that the present invention may be useful in treating other lower body cavity ailments, particularly post surgical and surgical treatments to enhance sterilization and incision wound healing. The treatment of other ailments on which the present invention carbon dioxide and saline non-nasal delivery methods and treatments is effective are considered to be within the scope of the invention. This is especially true with respect to those dosages of the present invention that further include additional active components wherein the components have their own health benefits, and, as such are used to treat their targeted ailments.

Turning now to FIG. 3, a block diagram, block 30, shows the durations of therapeutic lower body cavity dosage used in some embodiments of the present invention carbon dioxide and saline lower body cavity delivery methods and treatments. The durations listed in FIG. 3 are ranges, so the actual duration can be any value including or between the low end of the range and the high end of the range, inclusive. In some embodiments of the present invention, the duration 29 lasts between 0.5 and 20 seconds. In other embodiments of the present invention, the duration 31 lasts between 2 and 15 seconds. In still other embodiments of the present invention, the duration 33 lasts between 5 and 10 seconds. Durations of more than 20 seconds are also considered to be within the scope of the invention.

Figure 4:
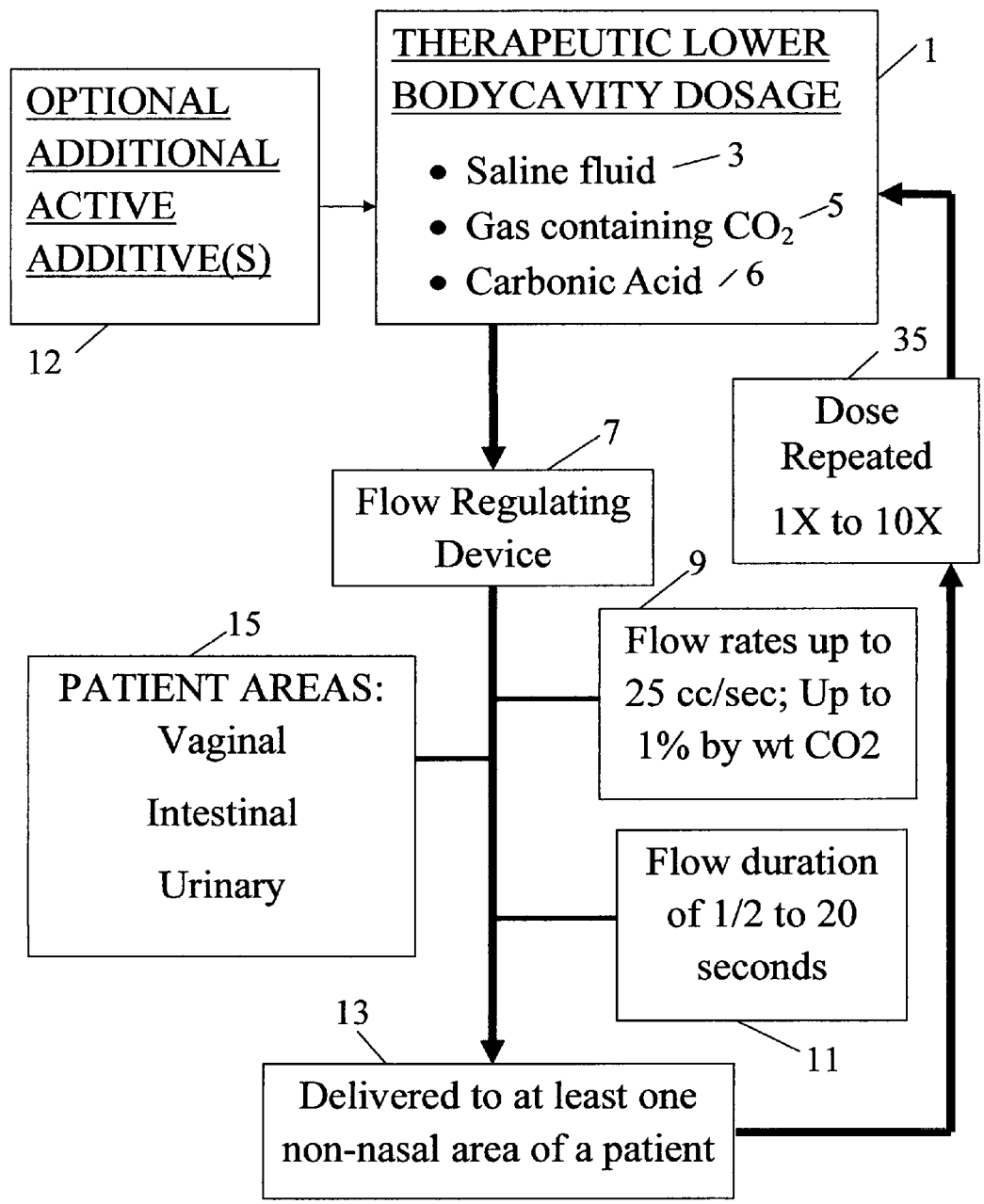
FIG. 4 is a block diagram of another embodiment of the present invention device carbon dioxide, carbonic acid and saline lower body cavity delivery methods and treatments, showing the additional step of repeating the other steps.

Turning now to FIG. 4, another embodiment of the present invention device carbon dioxide and saline delivery methods and treatments is shown. FIG. 4 is a block diagram of an embodiment of the present invention carbon dioxide, carbonic acid and saline delivery methods and treatments that incorporates many aspects shown in FIG. 1, and identical blocks are identically numbered. FIG. 4 illustrates the same diagram method steps, as in FIG. 1, except that here the dose is repeated 35. In some preferred embodiments, the dose is repeated 35 between one and ten times. In still other embodiments, the dose is repeated more than ten times. The step 35 of repeating the dose can be used if a single application of the therapeutic dosage 1 is insufficient to alleviate the ailments from which the patient suffers. Because the present invention has numerous applications including, but not limited to, daily cleansing, event cleansing, wound treatments, medicine delivery, infection treatments, etc., the number of repeat dosing may also depend on the intended purpose. For example, if daily cleansing is intended, only a single dose is usually sufficient. On the other hand, if a patient has had severe ailments, or has had an outbreak of infection, multiple dosing is recommended for more effective relief.

Turning now to FIG. 5, a block diagram, block 50, shows flow rates used in some embodiments of the present invention device carbon dioxide, carbonic acid and saline delivery methods and treatments. The flow rates used in FIG. 5 are shown as ranges, and the actual rate of the flow may any value between the low end of the range and the high end of the range, inclusive. In this Figure, these rates are for saline, carbonic acid and carbon dioxide, as well as the embodiments that include one or more other actives. The rates are the same as those elaborated upon supra. Ten cc per second is desirable for wound care and surgical flushing.

Turning now to FIG. 6, a block diagram, block 60, shows levels of carbon dioxide in the present invention dosages, based on the total weight of all of the dosage constituents, including additives, if present. These ranges are: not exceeding 1%; 0.05 to 1.0%; 0.2 to 0.8%; and) 0.2 to 0.6%.

Figure 7:
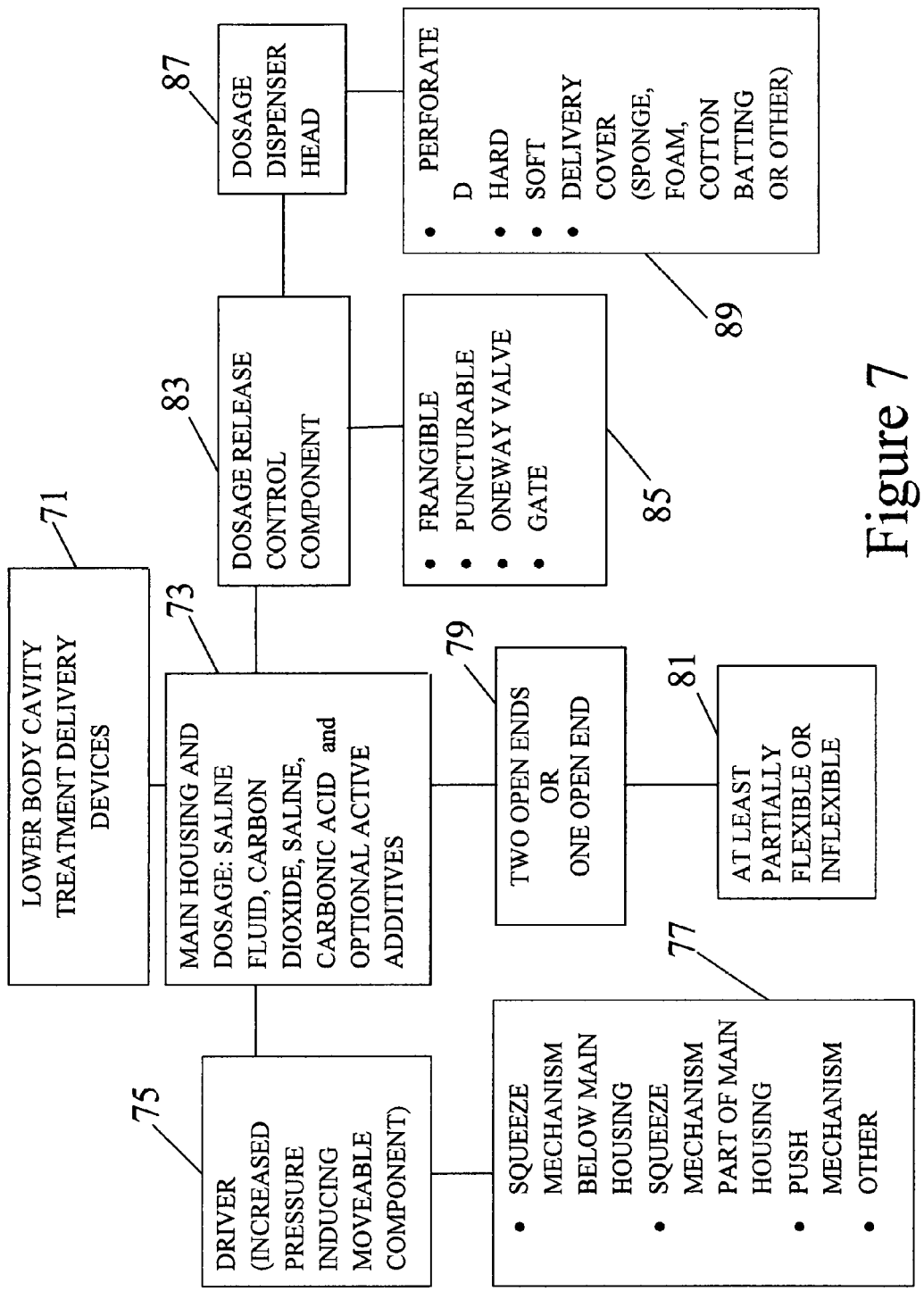
FIG. 7 illustrates a diagrammatic view of various present invention treatment lower body cavity delivery device components and options.

FIG. 7 illustrates a block diagram showing lower body cavity treatment delivery devices that may be used in the present invention methods. Here, block 71 illustrates the caption of the Figure, namely, lower body cavity treatment delivery device. The present invention device 71 may be a single dose dispenser (monodose) with a pressure control valve for flow rate regulation. The rate of flow is set in accordance with the ranges set forth above. In the case of a monodose dispenser, the entire dose is dispensed, so that time of dispensing does not need to be controlled—it is just the controlled flow rate over time it takes to unload the dose. Thus, a monodose dispenser may controllably release a pressurized mixture of the carbon dioxide and the saline with or without the addition of actives, until it stops flowing. On the other hand, a plural or multidose dispenser may be used, and needs dispensing on/off control such as a spring return push mechanism/valve, otherwise the entire contents could be unnecessarily released in one shot.

The various types of mechanisms for driving the contents from the container to the treatment areas are represented as driver 75 and block 77 provides specific examples. These include squeeze mechanisms where the squeeze component or bulb is below the content so that external squeeze pressure forces out the content, much like a turkey baster; squeeze mechanisms where the squeeze component is the actual dose holding aspect of the container, like a decongestant squeeze spray container; push mechanisms that physically operate much like syringes but may have more complex internal aspects, such as piercers or counter-biased valving; and others, referring to any known controlled flow mechanism available to the artisan, e.g., a pressurized container with a push release mechanism. The preferred pressurized containers are bag-on-valve containers.

In FIG. 7, block 73 shows the main housing and dosage. It contains a dosage of saline fluid, carbonic acid and carbon dioxide, with or without other actives, according to parameters as more specifically set forth above. Block 79 shows that the main housing 73 may have two open ends or one open end. In the case of one open end, the top end would include the release control and dispenser head mechanisms, with a closed bottom. In the case of a main housing with two open ends, one end would have the release control and dispenser head mechanisms and the other end would contain a moveable drive mechanism such as a pressure release mechanism, a piercer or a plunger (drive piston). Block 81 shows that the main housing 73 may be at least partially flexible or it may be inflexible. If the driver is the squeezing of the main housing, it must be flexible. If the driver a moveable component attached to the main housing 71 (a push or squeeze mechanism), then the main housing 71 is preferably inflexible.

Block 83 shows the dosage release control component. Block 85 illustrates the options for the dosage release control component, which are: frangible, puncturable, one-way valve, or gate. Block 87 shows the dosage dispenser head, which Block 89 then shows the options for, which are: perforated, hard, soft, or delivery cover (sponge, foam, cotton batting, or other).

FIG. 8 illustrates a front partially cut view of one embodiment of a present invention treatment delivery device 90. It includes a main housing 91 with a top 93 having a hollow central area containing a dosage of the present invention medicine. This storage area may be the inside of the main housing, or it may be one or more subunits—compartments, capsules, tanks, pouches, etc, within the main housing. In this embodiment, the main housing 91 has attached to its distal end a dosage control component that is a spray release nozzle 95 that is set for prescribed flow rates within the ranges set forth in the present invention claims and as described above. Internal bag container 105 contains the liquid/gas mixture of the present invention and external pressure on bag 105 is created by pressurized gas located in space 107 inside main housing 91. At top 93 is a dosage dispenser head, in this case, a push dispenser mechanism 97 that includes release orifice 101, actuation tube 99 and push pad 103. A user places the push dispenser mechanism 97 near the patient area to be treated or inserted into the area of the patient to be treated, at its distal end (orifice 101) while delivery device 90 and then pressing push pad 103 to release the contents. The flow regulation is set to an acceptable range so as to be relatively gentle for the intended purpose. This may include ranges in the order of ½ cc/sec to 20 cc per second. Typically this is a multidose device wherein the user may be given instructions to dispense for a specified time period to the area to be treated, e.g., the eye, the mouth, the ear, etc. Alternatively, a built-in timer could automatically control the dose. For example, the device could have a slow spring closure that would require reset and re-push to reactivate.

FIG. 9 shows an alternative present invention treatment delivery device 110. This is a squeeze device that includes a main body 111 with flexible walls and a dispensing nozzle 115 at its top 113. There is a stop 117 and threads 109 and a tapered dispensing tip 119 designed for cavity insertion, but can readily be used without insertion, as a spray device to deliver dosages to the areas to be treated. There is a flow control valve 112 that regulates the rate of delivery. Additional valving, such as a duck bill valve, may also be included. The present invention liquid/gas mixture is contained within the main housing 111 and is dispensed by a user directing the device toward or into the area to be treated and squeezing.

FIG. 10 shows a front partially cut view of a present invention treatment delivery device 120 being held in a hand using two fingers and a thumb, as shown. There is a main housing 121 and a vertically moveable piston 131. A rigid, semi-flexible or flexible container or pouch 123 contains the liquid/gas mixture of the present invention and piercing tube 125 is connected to flow control valve 127. A user holds treatment delivery device 120 as shown, directs it toward the areas to be treated, pushes piston 131 upwardly to force pouch 123 to rupture via piercing tube 125 for medicine release through valve 127 to the treatment area or placing the device partially inside the treatment area of the patient or user.

FIGS. 11, 12 and 13 illustrate front partially cut views of one embodiment of a present invention treatment delivery device 150 with a frangible internal medicine capsule 171 containing medicine 175—the gas and liquid mixtures described above. Device 150 may be used for a monodose or multidose using replacement capsules. The three Figures show the device in different stages of use. Identical number is used for all three of the figures and the device 150 is described collectively for all of these figures.

Device 150 is a push device that relies upon a frangible capsule 171 to deliver the medicine 175 by breaking open the top 173 of the frangible capsule 171. Device 105 includes a main housing 151 designed with both an open top and an open bottom, as shown. Permanently inserted into the open top of main housing 151 is a dosage dispensing head 161, with release tube 165 and control valve 153. Dosage dispensing head 161 has a downward hemispherical end 163 for puncturing the top 173 (e.g., a foil top) of capsule 171. A circular platform or dual protrusions, such as platform 167, serves as a finger grip and is attached to main housing 151. Capsule 171 may be permanently installed in main housing 151, or it may be removably placed therein so that subsequent capsules may be inserted, the former being a monodose and the latter being a multidose device.

Further, capsule 171 may be fully frangible, but is preferably so only at its top 173. Capsule 171 could have different shape, such as a hemispherical bottom to correspond to the shape of the end 163 of the dosage dispensing head 161. Or both could have other shapes and be the same or different, e.g., a chisel shaped end/bottom. Plunger 157 has a sealed piston 159 at its distal end and a widened finger rest at its proximal end. Plunger 157 may be inserted at its distal end permanently or removably, and its piston 159 may be any shape, but is preferably the same or similar to the bottom of the capsule. The piston 159 is used to drive the capsule 171 into breaker end 163, as shown sequentially in FIGS. 11, 12 and 13. In FIG. 11, a user's thumb and first two fingers are shown embracing the plunger 157 and the platform 167, respectively. By placing the device 150 near and directing the device toward an area to be treated and pushing plunger 157 upwardly while holding the device steady, the frangible top 173 is broken and the gas/liquid medicine begins release from the device 150 (FIG. 12). The medicine is nearly fully expended by the time the plunger 157 is pushed maximally and the top 163 is near or at the bottom of the capsule 171 (FIG. 13), to deliver the medicine to the user effectively.

Figure 14:
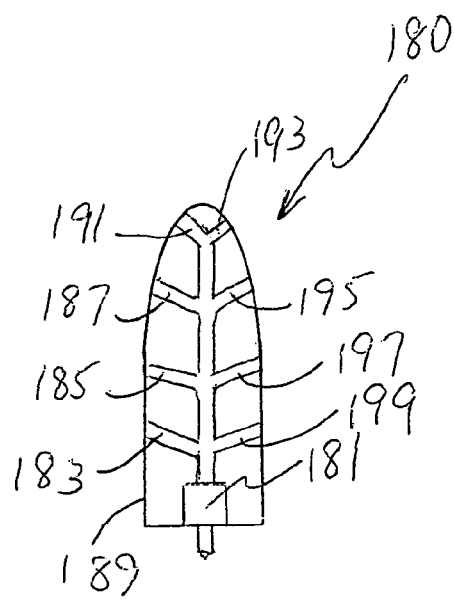
FIGS. 14 and 15 show alternative types of dosage dispenser heads that may be used in present invention lower body cavity devices, one showing multiple release ports and the other showing multiple release ports with a soft contact sheath.
Figure 15:
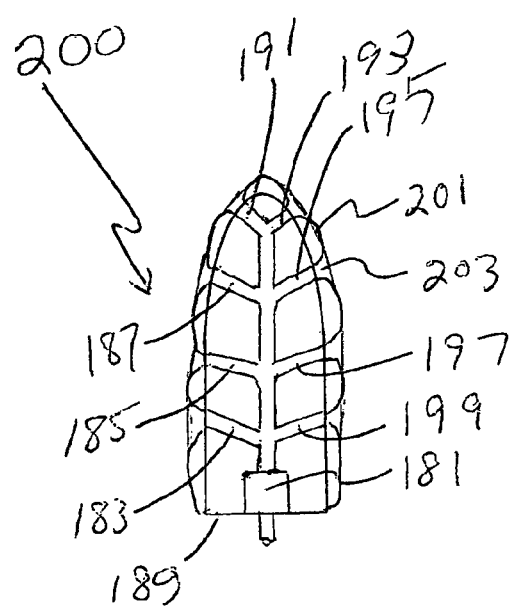
Figure 16:
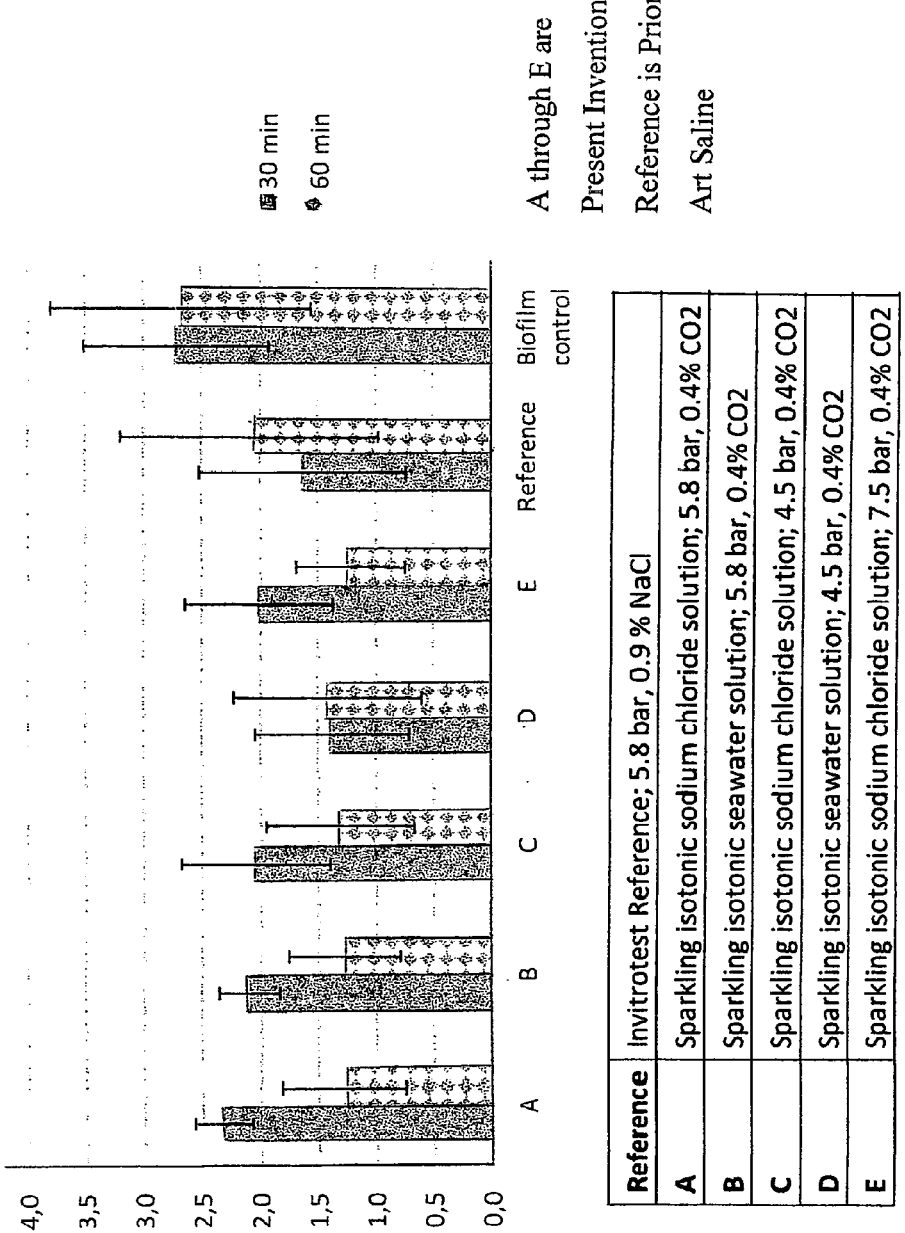
FIG. 16 is a graphic representation showing present invention dosages that are cleansing biofilms and killing bacteria after one hour versus regular saline treatment and no treatment; and, FIG. 17 is a block diagram of various embodiments of the present invention lower body cavity delivery device showing option extension arrangements for the present invention carbon dioxide, carbonic acid and saline methods and treatments.
Figure 17:
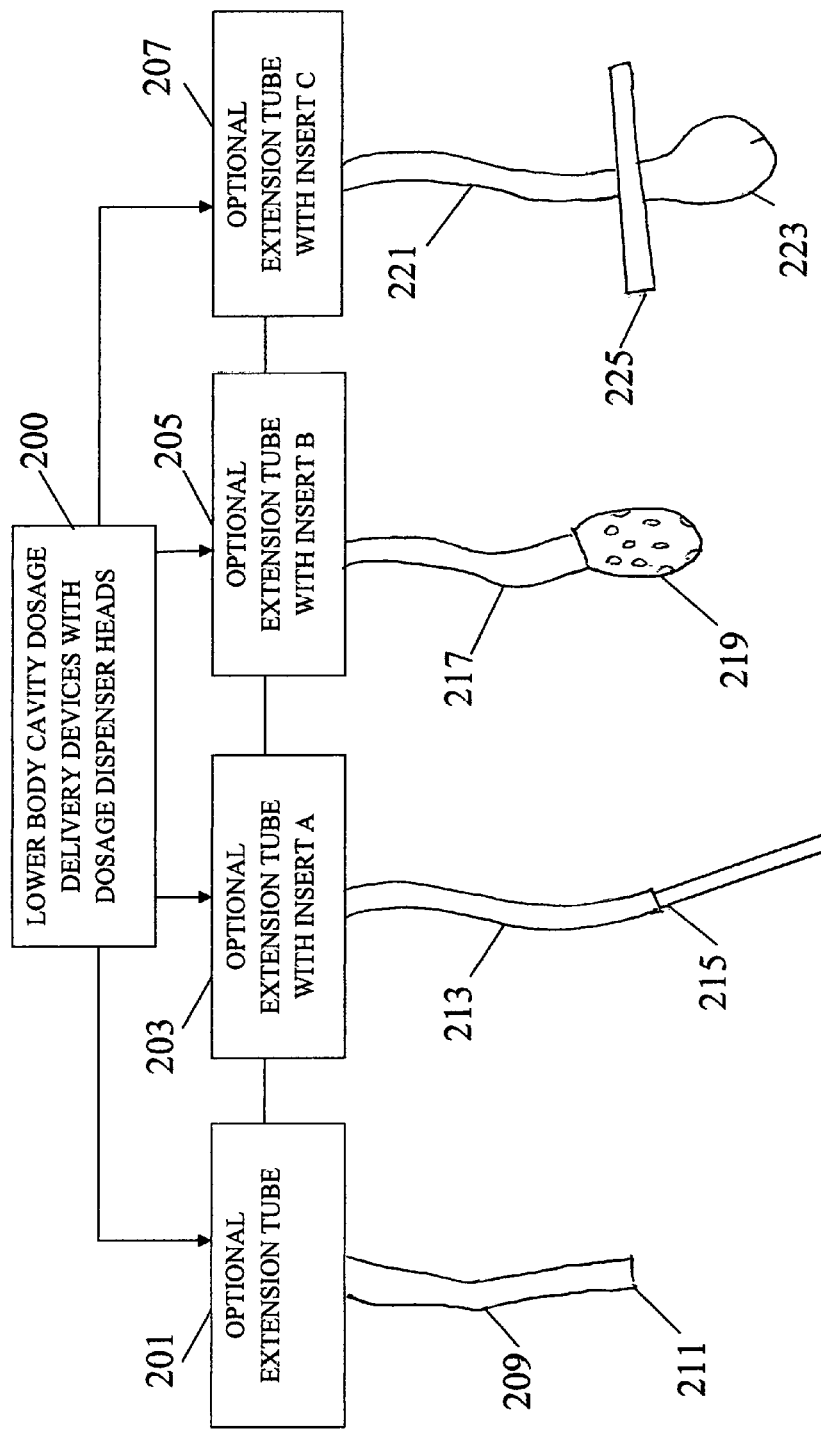

FIGS. 14 and 15 show alternative types of dosage dispenser heads that may be used in present invention device one has multiple release ports and the other has multiple release ports with a soft contact sheath. FIG. 14 shows a cut front view of one dosage dispenser head 180 that may be used in conjunction with a present invention device. It includes a control valve 181 to regulate release of medicine to be within the proscribed ranges set forth above. Upstream from control valve 181 is a main flow channel 183 with branches 185, 187, 189, 191,193 and 195 to show a diverse multiport manifold head for diverse. This dosage dispensing head will direct the gas/liquid medicine in many directions simultaneously to more evenly and quickly coat a treated area, such as a vaginal or intestinal or other cavity, involving or not involving surgery.

FIG. 15 shows a similar present invention dosage dispensing head 200, but with a soft pad for treatment area comfort. This pad does not cover the ports and may be made of soft pervious or impervious materials such as various foams or skins. Alternatively, they may be previous and cover the parts so as to create wetting foams or sponges to effect broad based medicine placement in the many diverse areas of treatment.

The ratio of carbon dioxide to salt may be any therapeutic amount. However, typically carbon dioxide saturated saline or close to saturation may be used. Alternatively, levels of carbon dioxide may be below saturation or supersaturated, as mentioned, and the levels of actives added to the solution are a matter of choice. In preferred preparation methods, the additive(s) are added to the saline and then the carbon dioxide is injected or otherwise added. Alternatively, the additives may be already in the solution and others may optionally be added, such as sea water with natural additives to which vitamins are further added.

In order to show the unexpected results of the present invention saline/carbon dioxide/carbonic acid (with or without additional active additives), consumer testing was conducted and very effective results were achieved. Nasal use was the treatment baseline as users could readily determine harshness or lack of harshness, as well as whether or not nasal passages were opened rapidly. While the use for nasal cavity treatments is the subject of a sister application of the present application, these tests did show wide, friendly acceptance of sparkling saline (saline with carbon dioxide). More than 85% in one set of testing and more than 90% in another favored the product. Only one testing consumer experienced slight stinging and no one experienced severe stinging as had occurred with carbon dioxide gas treatments as proscribed by the Capnia prior art to Rasor et al cited above. Additionally, biofilm testing was conducted to test the efficacy of the present invention beyond the use of nasal sprays, to determine efficacy for many uses.

FIG. 16 shows comparative graph bars for present invention sparkling saline products A, B, C, D and E, and for a reference product (conventional prior art saline without the carbon dioxide and carbonic acid of the present invention). The tests were performed by an independent testing lab and consistent biofilms (normalized to match) of staph bacteria (24 hour growth *s. aureus* biofilm). Identical spays of present invention products A through E and the Reference Prior Art saline (0.9% isotonic) were used in the experiment. The solid bars represent relative populations of the bacteria one half hour after treatment, and the dotted diamond bars represent relative populations of the bacteria after one hour. As can be seen, all of the present invention products A through E continued to kill or remove the bacterial threat after one hour and reduced bacterial population after one half hour and after one hour significantly as compared to the end bars (biofilm control, untreated). Further, using the Prior Art Saline, the population of bacteria rose significantly after one hour as compared to one half hour. Thus, saline does not appear to have any continuing efficacy after its mechanical cleansing, whereas the present invention products were still maintaining or lowering the low population of bacteria. In addition, color photographs of these samples showed significant browning of the otherwise live green colored bacteria, further supporting that the bacteria was not only removed by the present invention, but also partially destroyed biologically. These results are even more surprising; the present invention $CO_2$ levels are much lower than the proscribed prior art Rasor et al indicated levels of $CO_2$, yet significant efficacy has been achieved, as evidenced by both the consumer use testing and the laboratory testing. Further, these tests are about reducing bacteria and not nasal treatments. As such, the present invention applications for treating many areas and ailments is supported by these biofilm test results.

FIG. 17 is a block diagram of various embodiments of the present invention lower body cavity delivery devices with dosage dispenser heads 200, showing option extension arrangements for the present invention carbon dioxide, carbonic acid and saline methods and treatments. Optional extension tube 201 may be a flexible, semi-flexible or rigid tube and tube 209 is shown as flexible, with a distal end 211. Optional extension tube with insert A 203 includes a tube 213 with a rigid insertion or dilation tube 215, typically used for urinary tract treatments. Optional extension tube with insertion B 205 includes extension tube 217 with a spray tip 219 having a plurality of diversely directed spray orifices. Optional extension tube with insertion C includes an extension tube 221 with an end piece that has a bulbous protrusion 223 with a stop flange 225, typically for anal insertion.

Although particular embodiments of the invention have been described in detail herein with reference to the accompanying drawings, it is to be understood that the invention is not limited to those particular embodiments, and that various changes and modifications may be effected therein by one skilled in the art without departing from the scope or spirit of the invention as defined in the appended claims. For example, the term "additives" as used herein means any active component that exists with the saline other than the salt and the water. Thus, active additives refer to additional active components that are inherent or are added during preparation and have an additional function. For example, a solution from a natural spa would have micronutrients in addition to the salt and water. As another example, sea water may be purified and selectively reconstituted to have controlled levels of salt, as well as other natural additives, such as beneficial minerals and metals.

What is claimed is:

1. A method for treating or preventing lower body cavity ailments in a patient in need thereof, said method comprising:

directing a therapeutic, dosage to at least one lower body cavity area of said patient, through a flow regulating device having a flow channel, said dosage including: (a) a saline fluid, (b) dissolved carbon dioxide gas, (c) carbonic acid as an active antibacterial component, and (d) at least one additional active component, wherein the therapeutic, dosage is delivered at a flow rate through said flow channel of the combined saline fluid, carbon dioxide, carbonic acid and said at least one additional active component, does not exceed 25.0 cc per second, and the carbon dioxide therein does not exceed 1.0% by weight based on the entire weight of the dosage.

2. The method of claim 1, wherein said lower body cavity ailment is a vaginal area ailment.

3. The method of claim 1, wherein said ailment is an intestinal ailment.

4. The method of claim 1, when said ailment is an urinary tract ailment.

5. The method of claim 1, wherein said flow regulating device is selected from the group consisting of a single dose dispenser with a pressure control valve for released flow regulation and a multiple dose dispenser with a pressure control valve for released flow regulation, and said multiple dose dispenser further includes a dosage amount control mechanism and activator to limit dosage release amount for each activation.

6. The method of claim 5 wherein said dispenser further includes an extension tube and distal end outlet.

7. The method of claim 6 wherein said distal end outlet includes a body cavity insert.

8. The method of claim 7 wherein said insert includes a bulbous portion and a stop flange.

9. The method of claim 1, wherein the duration of spraying each dosage is ½ to 20 seconds.

10. The method of claim 1, wherein the dose is repeated from 1 to 10 times.

11. The method of claim 1, wherein said flow rate through said flow channel of the combined saline fluid, carbon dioxide, carbonic acid and said at least one additional active component is in the range of 0.2 cc per second to 10.0 cc per second and the carbon dioxide therein is in the range of 0.05% to 1.0% by weight based on the entire weight of the dosage.

12. The method of claim 1, wherein said flow rate through said flow channel of the combined saline fluid, carbon dioxide, carbonic acid and said at least one additional active component is in the range of 0.4 cc per second to 4.0 cc per second and the carbon dioxide therein is in the range of 0.2% to 0.8% by weight based on the entire weight of the dosage.

13. The method of claim 1, wherein said flow rate through said flow channel of the combined saline fluid, carbon dioxide, carbonic acid and said at least one additional active component is in the range of 0.4 cc per second to 2 cc per second and the carbon dioxide therein is in the range of 0.2% to 0.6% by weight based on the entire weight of the dosage.

14. A method for treating or preventing lower body cavity ailments in a patient in need thereof, said method comprising:
directing a therapeutic, dosage to at least one lower body cavity area of said patient, through a flow regulating device having a flow channel, said dosage including: (a) a saline fluid, (b) dissolved carbon dioxide gas, and (c) carbonic acid as an active antibacterial component, wherein the therapeutic, non-inhaled dosage is delivered at a flow rate through said flow channel of the combined saline fluid and gaseous carbon dioxide does not exceed 5.0 cc per second and the carbon dioxide therein does not exceed 1.0% by weight based on the entire weight of the dosage.

15. The method of claim 14, wherein said lower body cavity ailment is a vaginal area ailment.

16. The method of claim 14, wherein said ailment is an intestinal ailment.

17. The method of claim 14, when said ailment is an urinary tract ailment.

18. The method of claim 14, wherein said flow regulating device is selected from the group consisting of a single dose dispenser with a pressure control valve for released flow regulation and a multiple dose dispenser with a pressure control valve for released flow regulation, and said multiple dose dispenser further includes a dosage amount control mechanism and activator to limit dosage release amount for each activation.

19. The method of claim 18 wherein said dispenser further includes an extension tube and distal end outlet.

20. The method of claim 19 wherein said distal end outlet includes a body cavity insert.

21. The method of claim 20 wherein said insert includes a bulbous portion and a stop flange.

22. The method of claim 14, wherein the duration of spraying each dosage is ½ to 20 seconds.

23. The method of claim 14, wherein said flow regulating device is a multiple dose dispenser with a pressure control valve for released flow regulation and said multiple dose dispenser further includes a dosage amount control mechanism and activator to limit dosage release amount for each activation.

24. The method of claim 14, wherein said flow rate through said flow channel of the combined saline fluid, carbon dioxide, carbonic acid and said at least one additional active component is in the range of 0.2 cc per second to 10.0 cc per second and the carbon dioxide therein is in the range of 0.05% to 1.0% by weight based on the entire weight of the dosage.

25. The method of claim 14, wherein said flow rate through said flow channel of the combined saline fluid, carbon dioxide, carbonic acid and said at least one additional active component is in the range of 0.4 cc per second to 4.0 cc per second and the carbon dioxide therein is in the range of 0.2% to 0.8% by weight based on the entire weight of the dosage.

26. The method of claim 14, wherein said flow rate through said flow channel of the combined saline fluid, carbon dioxide, carbonic acid and said at least one additional active component is in the range of 0.4 cc per second to 2 cc per second and the carbon dioxide therein is in the range of 0.2% to 0.6% by weight based on the entire weight of the dosage.

* * * * *